BEGIN

(12) United States Patent
Laredo

(10) Patent No.: US 7,947,849 B2
(45) Date of Patent: May 24, 2011

(54) UV-ABSORBERS FOR OPHTHALMIC LENS MATERIALS

(75) Inventor: Walter R. Laredo, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 12/915,990

(22) Filed: Oct. 29, 2010

(65) Prior Publication Data

US 2011/0046259 A1 Feb. 24, 2011

Related U.S. Application Data

(62) Division of application No. 12/435,994, filed on May 5, 2009, now Pat. No. 7,884,228.

(60) Provisional application No. 61/050,828, filed on May 6, 2008.

(51) Int. Cl.
*C07C 69/52* (2006.01)
(52) U.S. Cl. .................. 560/205; 560/221; 623/6.11
(58) Field of Classification Search .................. None
See application file for complete search history.

(56) References Cited

U.S. PATENT DOCUMENTS

| | | | |
|---|---|---|---|
| 5,290,892 A | 3/1994 | Namdaran et al. |
| 5,331,073 A | 7/1994 | Weinschenk, III et al. |
| 5,470,932 A | 11/1995 | Jinkerson |
| 5,487,885 A | 1/1996 | Sovak et al. |
| 5,543,504 A | 8/1996 | Jinkerson |
| 5,693,095 A | 12/1997 | Freeman et al. |
| 5,741,924 A | 4/1998 | Sovak et al. |
| 6,015,874 A | 1/2000 | Hiratani |
| 6,166,218 A | 12/2000 | Ravichandran et al. |
| 6,528,602 B1 | 3/2003 | Freeman et al. |
| 6,806,337 B2 | 10/2004 | Schlueter et al. |
| 6,846,897 B2 | 1/2005 | Salamone et al. |
| 6,852,793 B2 | 2/2005 | Salamone et al. |
| 6,872,793 B1 | 3/2005 | Schlueter |
| 7,037,954 B2 | 5/2006 | Baba et al. |
| 7,067,602 B2 | 6/2006 | Benz et al. |
| 7,101,949 B2 | 9/2006 | Salamone et al. |
| 7,278,737 B2 | 10/2007 | Mainster et al. |
| 7,326,423 B2 | 2/2008 | Pearson et al. |
| 2006/0115516 A1 | 6/2006 | Pearson et al. |
| 2007/0092830 A1 | 4/2007 | Lai et al. |
| 2007/0092831 A1 | 4/2007 | Lai et al. |
| 2008/0242818 A1 | 10/2008 | Benz et al. |

FOREIGN PATENT DOCUMENTS

| | | |
|---|---|---|
| CN | 17277338 | 2/2006 |
| EP | 25331 A * | 3/1981 |
| EP | 0455058 A2 | 11/1991 |
| EP | 1033590 B1 | 6/2000 |
| EP | 0913713 B1 | 12/2002 |
| JP | 40021535 B4 * | 9/1964 |
| JP | 08176139 | 7/1996 |
| JP | 2005053058 | 3/2005 |
| JP | 2009013148 | 1/2009 |
| WO | WO9414410 A1 | 7/1994 |
| WO | WO9830900 A2 | 7/1998 |
| WO | WO2006057824 A2 | 6/2006 |
| WO | WO2008109624 A2 | 9/2008 |

OTHER PUBLICATIONS

Kador, et al., "Identification of an Aldose Reductase Inhibitor Site by Affinity Labeling," Biorganic & Medicinal Chemistry, 1995, pp. 1313-1324, vol. 3, No. 10.
Kador, et al., "Irreversible aldose reductase inhibitors," Enzymology and Molecular Biology of Carbonyl Metabolism, 1987, pp. 353-365.

* cited by examiner

*Primary Examiner* — Sudhakar Katakam
(74) *Attorney, Agent, or Firm* — Patrick M. Ryan

(57) ABSTRACT

UV absorbing monomers that are particularly useful in ophthalmic devices are disclosed.

15 Claims, 9 Drawing Sheets

1H NMR Spectra
1,2-dimethoxy-4-(2-nitroprop-1-enyl)benzene (Example 3)

1H NMR Spectra 1,2,3-trimethoxy-5-(2-nitroprop-1-enyl)benzene (Example 4)

1H NMR Spectra 2-(2-methoxy-4-(2-nitroprop-1-enyl)phenoxy)ethanol (Example 6)

5-(2-Nitroprop-1-enyl)benzo[d][1,3]dioxole (Example 1) in Chloroform (10 mm Path Length)

5-(2-Nitroprop-1-enyl)benzo[d][1,3]dioxole (Example 1) in Unextracted Test Samples (0.9 mm Path Length)

1-chloro-4-(2-nitroprop-1-enyl)benzene (Example 2) In Unextracted Test Samples (0.9 mm Path Length)

1,2-dimethoxy-4-(2-nitroprop-1-enyl)benzene (Example 3) In Unextracted Test Samples (0.9 mm Path Length)

2-(2-methoxy-4-(2-nitroprop-1-enyl)phenoxy)ethyl methacrylate (Example 7) In Non-extracted And Extracted Test Samples (0.9 mm Path Length)

UV-ABSORBERS FOR OPHTHALMIC LENS MATERIALS

CROSS-REFERENCE TO RELATED APPLICATIONS

This application is a divisional application of U.S. Ser. No. 12/435,994, filed May 5, 2009, which claims priority to U.S. Provisional Application, U.S. Ser. No. 61/050,828, filed May 6, 2008.

FIELD OF THE INVENTION

This invention is directed to ophthalmic lens materials. In particular, this invention relates to ultraviolet light absorbers that are suitable for use in ophthalmic lens materials.

BACKGROUND OF THE INVENTION

Many UV light absorbers are known as ingredients for polymeric materials used to make ophthalmic lenses. UV absorbers are preferably covalently bound to the polymeric network of the lens material instead of simply physically entrapped in the material to prevent the absorber from migrating, phase separating or leaching out of the lens material. Such stability is particularly important for implantable ophthalmic lenses where the leaching of the UV absorber may present both toxicological issues and lead to the loss of UV blocking activity in the implant.

Numerous copolymerizable benzatriazole, benzophenone and triazine UV absorbers are known. Many of these UV absorbers contain conventional olefinic polymerizable groups, such as methacrylate, acrylate, methacrylamide, acrylamide or styrene groups. Copolymerization with other ingredients in the lens materials, typically with a radical initiator, incorporates the UV absorbers into the resulting polymer chain. Incorporation of additional functional groups on a UV absorber may influence one or more of the UV absorber's UV absorbing properties, solubility or reactivity. If the UV absorber does not have sufficient solubility in the remainder of the ophthalmic lens material ingredients or polymeric lens material, the UV absorber may coalesce into domains that could interact with light and result in decreased optical clarity of the lens.

Examples of polymeric ophthalmic lens materials that incorporate UV absorbers can be found in U.S. Pat. Nos. 5,290,892; 5,331,073 and 5,693,095.

In addition to blocking UV light, some ophthalmic lenses also block blue light. See, for example, U.S. Pat. Nos. 5,470,932 and 5,543,504. These lenses block both types of light by using two chromophores: a UV absorber and a yellow dye.

There is a need for UV absorbers that are capable of blocking not only UV light (400 nm and below) but also blocking at least some light in the 400-450 nm range.

SUMMARY OF THE INVENTION

The present invention provides UV absorbers that block not only UV light but also light in the 400-450 nm range. These UV absorbers are suitable for use in ophthalmic devices, including contact lenses, and are particularly useful in implantable lenses, such as intraocular lenses (IOLs). The UV absorbers of the present invention are copolymerizable with other ingredients in ophthalmic device formulations.

The UV absorbers of the present invention provide the following benefits. They absorb wavelengths of light between 400-450 nm in addition to UVA rays between 400-320 nm, UVB rays between 320-280 nm, and UVC rays below 280 nm. They also contain reactive groups, which allow for covalent attachment of the UV absorber to the ophthalmic lens material. Finally, the UV absorbers of the present invention can be readily synthesized in relatively simple steps (e.g., 2-4) from relatively inexpensive starting materials.

BRIEF DESCRIPTION OF THE DRAWINGS

FIGS. 7-11 show the UV/VIS spectra of test lens materials containing various UV absorbers.

DETAILED DESCRIPTION OF THE INVENTION

Figure 1:
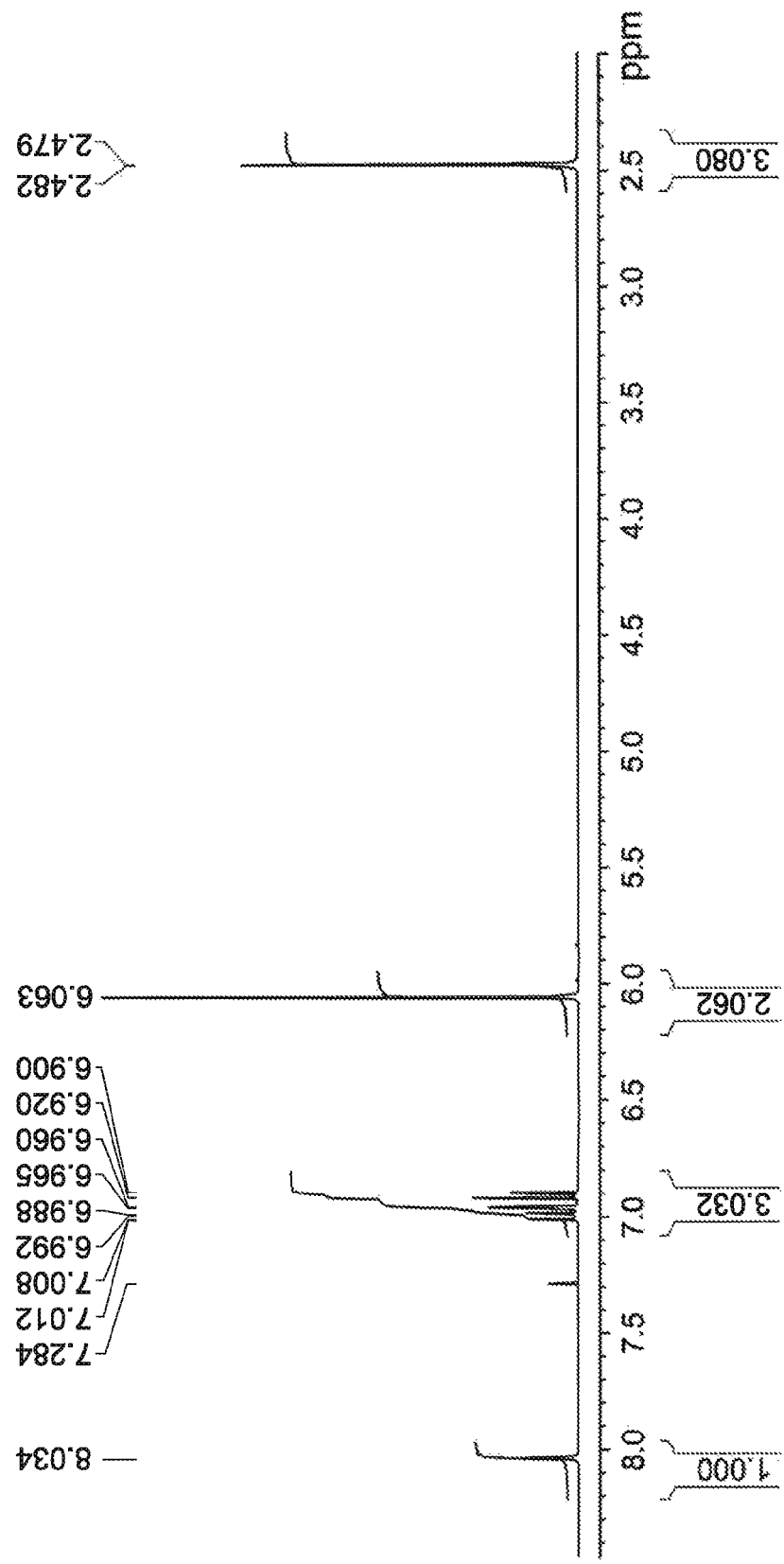
FIGS. 1-7 show the 1H NMR spectra for the compounds of Examples 1-4, 6, and 7, respectively.

Unless indicated otherwise, all ingredient amounts expressed in percentage terms are presented as % w/w.

The UV absorbers of the present invention have the structure shown in formula I.

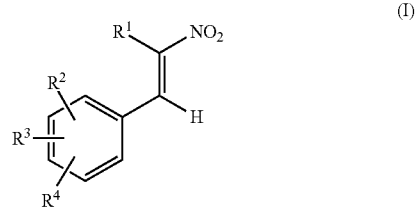

(I)

wherein:
$R^1$=H, $CH_3$, $CH_3CH_2$, $(CH_3)_2CH$, $CH_3CH_2CH_2$, $HOCH_2$, $CH_2F$, $(CH_3)_3C$, $(CH_3)_3COCH_2$, $HOC(O)$ $CHOCH_3$, $C(O)OH$, $CH_3OC(O)CHNH_2CH_2$, $CH_3CH_2OC(O)(CH_2)_2$, $(CH_3O)_2CH$, $(CH_3)_2CHOC(O)$, $CH_3CH_2OC(O)$, $CH_3OC(O)$, $(CH_3CH_2O)_2CH$, $CH_3OC(O)(CH_2)_2$, $CH_3OC(O)CH_2NHCH_2$, $CH_3CH_2OC(O)CH_2$, $C_6H_5OH$, $C_6H_4OH$, $C_6H_5CH_2$, $C_6H_4CNCH_2$, $C_6H_4NO_2$, $C_6H_4NH_2CH_2$, $CH_2CH_2CHOC(O)$, $CH_2$=$CHC(O)OCH_2$, $CH_2$=$CCH_3C(O)OCH_2$, $CH_2$=$CHC(O)OCH_2CH_2NHC(O)$, $CH_2$=$CCH_3C(O)OCH_2CH_2NHC(O)$, $CH_2$=$CHC(O)OCH_2CH_2NHC(O)OCH_2$, or $CH_2$=$CCH_3C(O)OCH_2CH_2NHC(O)OCH_2$;

$R^2$, $R^3$ and $R^4$ independently =H, OH, $CH_3O$, $CH_3CH_2O$, $CH_3CH_2CH_2O$, $(CH_3)_2CHO$, $(CH_3)_3CO$, $CH_3C(O)O$, $C_6H_5CH_2O$, $HOCH_2CH_2O$, $HOCH_2CH_2CH_2O$, $CH_2$=$CHC(O)OCH_2CH_2O$, or $CH_2$=$CCH_3C(O)OCH_2CH_2O$, $CH_2$=$CCH_3C(O)O$, $CH_2$=$CHC(O)O$, $CH_2$=$CHC(O)OCH_2CH_2NHC(O)$, $CH_2$=$CCH_3C(O)OCH_2CH_2NHC(O)OCH_2CH_2O$, or $CH_2$=$CCH_3C(O)OCH_2CH_2NHC(O)OCH_2CH_2O$; or $R^2$=H and $R^3$ and $R^4$ taken together form a methylenedioxy group (as in Example 1); and provided that at least one of $R^1$, $R^2$, $R^3$, and $R^4$ must contain a methacrylate, acrylate, methacrylamide or acrylamide moiety.

The UV absorbers of formula I can be made via condensation reactions whereby benzaldehyde derivatives undergo Knoevenagel-type reactions with compounds having suitable active hydrogens. This results in the elimination of water and formation of the product, generally called a conjugated enone. For example, the UV absorbers can be synthesized via the condensation of a benzaldehyde derivative with a nitro alkyl compound containing 2 or 3 active hydrogen atoms on the same position as the nitro group, as shown below. The reaction is carried out using a base or suitable condensing agent that facilitates the elimination of water and drives the reaction forward. The resultant product is a conjugated enone, also referred to as a (2-nitrovinyl)benzene derivative generally drawn as formula I.

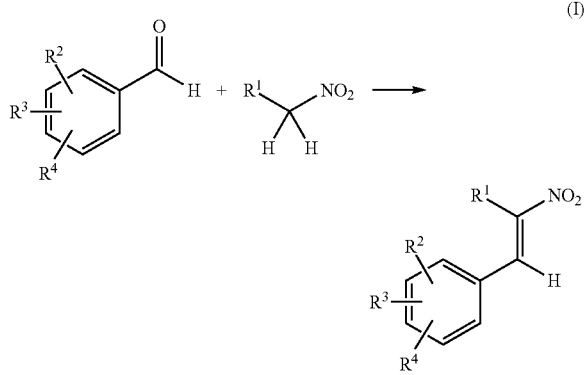

The UV absorbers of the present invention contain a reactive group that is capable of forming a covalent bond when reacted with vinyl monomers, co-monomers, macromers, crosslinking agents, and other reactive additives which are typically used in making polymer-based ophthalmic device materials. The reactive groups are preferably acrylate, methacrylate, acrylamide, or methacrylamide based, which are capable of reacting with vinyl monomers. The reactive groups can be positioned on either side of the conjugated enone C=C double bond as shown in representative structures 2 and 3

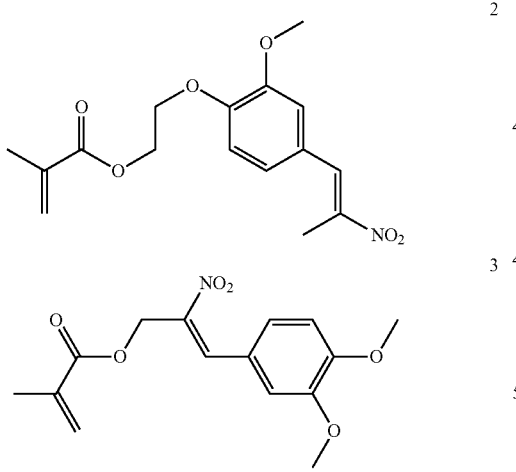

Preferred UV absorbers of formula I are those wherein:
$R^1$=H, $CH_3$, $HOCH_2$, $CH_3CH_2OC(O)$, $CH_2$=$CHC(O)OCH_2$, $CH_2$=$CCH_3C(O)OCH_2$, or $CH_2$=$CHC(O)OCH_2CH_2NHC(O)$, $CH_2$=$CCH_3C(O)OCH_2CH_2NHC(O)$;
$R^2$, $R^3$, and $R^4$ independently =H, OH, $CH_3O$, $CH_3CH_2O$, $CH_3C(O)O$, $C_6H_5CH_2O$, $CH_2$=$CHC(O)OCH_2CH_2O$, or $CH_2$=$CCH_3C(O)OCH_2CH_2O$; or $R^2$=H and $R^3$ and $R^4$ taken together form a methylenedioxy group; and
provided that only one of $R^1$, $R^2$, $R^3$, and $R^4$ contains a methacrylate, acrylate, methacrylamide or acrylamide moiety.

In one embodiment, $R^1$ contains a methacrylate, acrylate, methacrylamide or acrylamide moiety, and suitable $R^2$, $R^3$ and $R^4$ groups include, but are not limited to: 2,3-(methylenedioxy); 3,4-(methylenedioxy); 2-hydroxy-3-methoxy; 4-hydroxy-3-methoxy; 4-benzyloxy-3-methoxy; 4-acetoxy-3-methoxy; 3-ethoxy-4-hydroxy; 3-hydroxy-4-methoxy; 2-hydroxy-4-methoxy; 2-hydroxy-5-methoxy; 4-hydroxy-2-methoxy; 3,5-dimethoxy-4-hydroxy; 3,4-dibenzyloxybenzaldehyde; 3-benzyloxy-4-methoxy; 2,3-dimethoxy; 2,4-dimethoxy; 2,5-dimethoxy; 2,6-dimethoxy; 3,4-dimethoxy; 3,5-dimethoxy; 4-acetoxy-3,5-dimethoxy; 2,3,4-trimethoxy; 2,4,5-trimethoxy; 2,4,6-trimethoxy; and 3,4,5-trimethoxy.

An especially preferred UV absorber of formula I is 2-(2-methoxy-4-(2-nitroprop-1-enyl)phenoxy)ethyl methacrylate (structure 2 above).

The UV absorbers of the present invention are particularly suitable for use in IOLs. IOL materials will generally contain from 0.1 to 5% (w/w) of a UV absorber of formula I. Preferably, IOL materials will contain from 0.1 to 2% (w/w) of a UV absorber of the present invention. In one preferred embodiment, IOL materials contain an amount of a UV absorber of formula I sufficient to cause (by itself or in combination with other chromophores contained in the device material) the resulting device material to have the following light transmission properties: the light transmitted through a thin slab of the material (~1 mm thick) at 10% transmission is most preferably between 420-445 nm and at 50% transmission is between 425-455 nm.

Ophthalmic device materials are prepared by copolymerizing the UV absorbers of the present invention with other ingredients, such as device-forming materials, cross-linking agents, and blue-light blocking chromophores.

Many device-forming monomers are known in the art and include both acrylic and silicone-containing monomers among others. See, for example, U.S. Pat. Nos. 7,101,949; 7,067,602; 7,037,954; 6,872,793; 6,852,793; 6,846,897; 6,806,337; 6,528,602; and 5,693,095. In the case of IOLs, any known IOL device material is suitable for use in the compositions of the present invention. Preferably, the ophthalmic device materials comprise an acrylic or methacrylic device-forming monomer. More preferably, the device-forming monomers comprise a monomer of formula II:

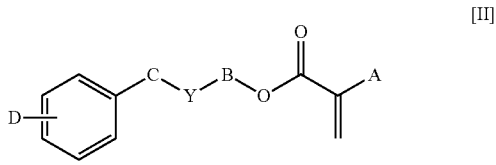

where in formula [II]:
A is H, $CH_3$, $CH_2CH_3$, or $CH_2OH$;
B is $(CH_2)_m$ or $[O(CH_2)_2]_z$;
C is $(CH_2)_w$;
m is 2-6;
z is 1-10;
Y is nothing, O, S, or NR', provided that if Y is O, S, or NR', then B is $(CH_2)_m$;
R' is H, $CH_3$, $C_nH_{2n'+1}$ (n'=1-10), iso-$OC_3H_7$, $C_6H_5$, or $CH_2C_6H_5$;
w is 0-6, provided that m+w≦8; and
D is H, $C_1$-$C_4$ alkyl, $C_1$-$C_4$ alkoxy, $C_6H_5$, $CH_2C_6H_5$ or halogen.

Preferred monomers of formula II are those wherein A is H or $CH_3$, B is $(CH_2)_m$, m is 2-5, Y is nothing or O, w is 0-1, and D is H. Most preferred are 2-phenylethyl methacrylate; 4-phenylbutyl methacrylate; 5-phenylpentyl methacrylate;

2-benzyloxyethyl methacrylate; and 3-benzyloxypropyl methacrylate; and their corresponding acrylates.

Monomers of formula II are known and can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding methacrylic acid to the conjugate alcohol and catalyzing with a carbodiimide or mixing the conjugate alcohol with methacryloyl chloride and a base such as pyridine or triethylamine.

Device materials generally comprise a total of at least about 75%, preferably at least about 80%, of device-forming monomers.

In addition to a UV absorber of formula I and a device-forming monomer, the device materials of the present invention generally comprise a cross-linking agent. The cross-linking agent used in the device materials of this invention may be any terminally ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2$=$C(CH_3)C$(=$O$)$O$—$(CH_2CH_2O)_p$—$C$(=$O$)$C(CH_3)$=$CH_2$ where p=1-50; and $CH_2$=$C(CH_3)C$(=$O$)$O(CH_2)_tO$—$C$(=$O$)$C(CH_3)$=$CH_2$ where t=3-20; and their corresponding acrylates. A preferred cross-linking monomer is $CH_2$=$C(CH_3)C$(=$O$)$O$—$(CH_2CH_2O)_p$—$C$(=$O$)$C(CH_3)$=$CH_2$ where p is such that the number-average molecular weight is about 400, about 600, or about 1000.

Generally, the total amount of the cross-linking component is at least 0.1% by weight and, depending on the identity and concentration of the remaining components and the desired physical properties, can range to about 20% by weight. The preferred concentration range for the cross-linking component is 0.1-17% (w/w).

Suitable polymerization initiators for device materials containing a UV absorber of the present invention include thermal initiators and photoinitiators. Preferred thermal initiators include peroxy free-radical initiators, such as t-butyl (peroxy-2-ethyl)hexanoate and di-(tert-butylcyclohexyl) peroxydicarbonate (commercially available as Perkadox® 16 from Akzo Chemicals Inc., Chicago, Ill.) and azo initiators, such as 1,1'-azobis(cyclohexanecarbonitrile) and 2,2'-azobis(2-methylpropionitrile) (AIBN) (commercially available as VAZO® catalyst 88 free radical source and VAZO® catalyst 64 free radical source, respectively, from Dupont, Wilmington, Del.). Initiators are typically present in an amount of about 5% (w/w) or less. Because free-radical initiators do not become chemically a part of the polymers formed, the total amount of initiator is customarily not included when determining the amounts of other ingredients.

The device materials containing a UV absorber of the present invention may also contain a reactive colorant. Suitable reactive blue-light absorbing compounds include those described in U.S. Pat. No. 5,470,932. Blue-light absorbers are typically present in an amount from about 0.01-0.5% (weight).

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use in other ophthalmic devices, such as contact lenses, keratoprostheses, and corneal inlays or rings.

The invention will be further illustrated by the following examples, which are intended to be illustrative, but not limiting.

Example 1

Preparation of 5-(2-nitroprop-1-enyl)benzo[d][1,3]dioxole

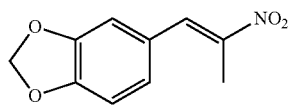

5.00 g (33.3 mmol) piperonal (Aldrich, Milwaukee, Wis.), 12.8 g (167 mmol) ammonium acetate (Fluke), and 50 g (670 Mmol) nitroethane, 98% (Aldrich) were combined in a 100 ml round bottom flask equipped with magnetic stirrer and nitrogen inlet. The reaction mixture was heated to 105° C. for 90 minutes and the solvent was removed under vacuum to give a dark yellow liquid which was recrystallized from cold methyl alcohol three times to give a yellow crystalline solid in 40% yield. 1H NMR spectra is shown in FIG. 1.

Example 2

Preparation of 1-chloro-4-(2-nitroprop-1-enyl)benzene

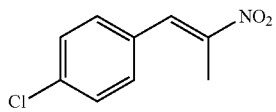

Figure 2:
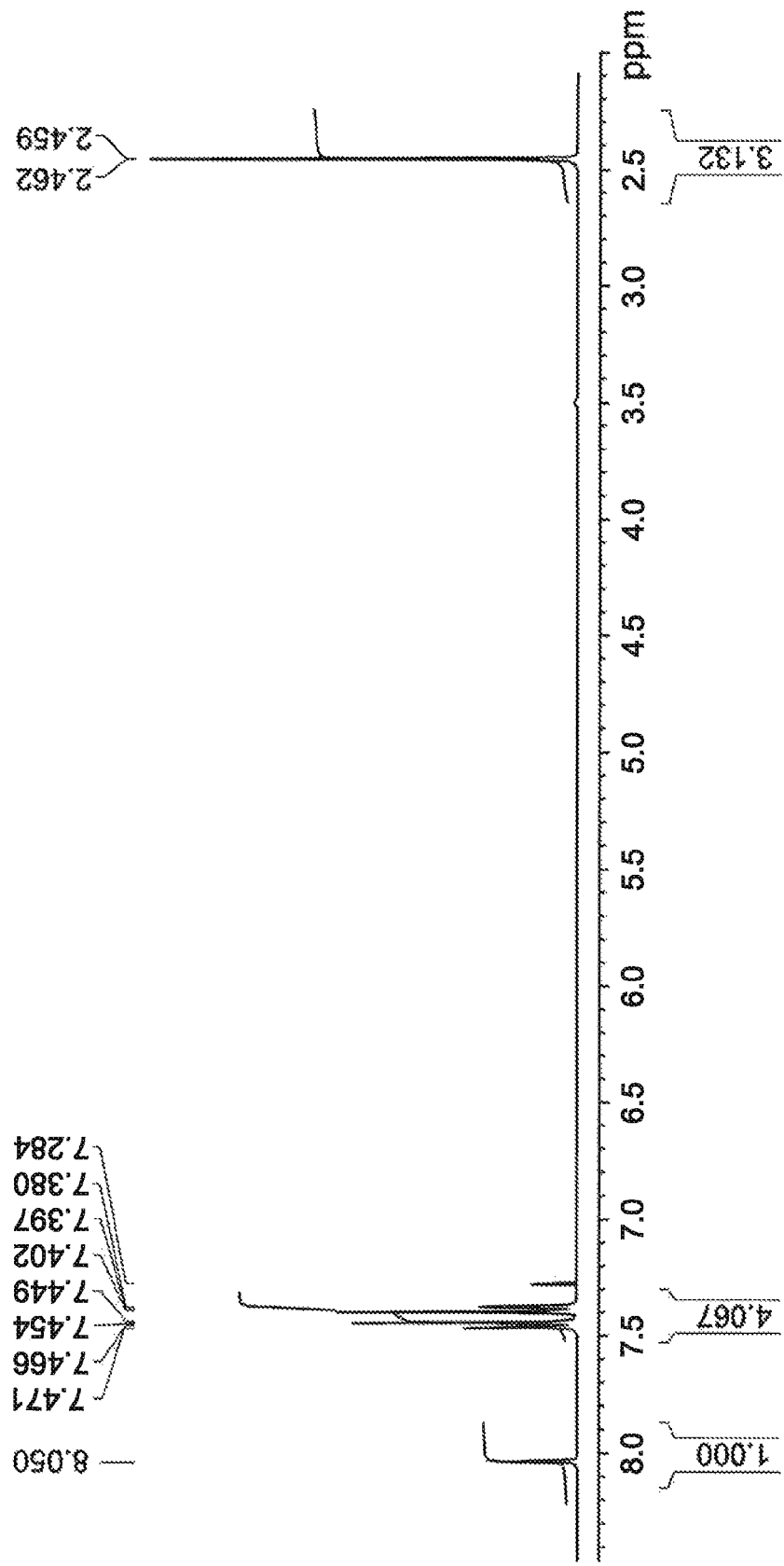

2.00 g (14.2 mmol) 4-chlorobenzaldehyde (Aldrich, Milwaukee, Wis.), 5.48 g (71.1 mmol) ammonium acetate (Fluka), and 50 g (666 Mmol) nitroethane, 98% (Aldrich) were combined in a 100 ml round bottom flask equipped with magnetic stirrer and nitrogen inlet. The reaction mixture was heated to 105° C. for 90 minutes and the solvent was removed under vacuum to give a dark yellow liquid which was recrystallized from cold methyl alcohol three times to give yellow needles in 40% yield. 1H NMR spectra is shown in FIG. 2.

Example 3

Preparation of 1,2-dimethoxy-4-(2-nitroprop-1-enyl)benzene

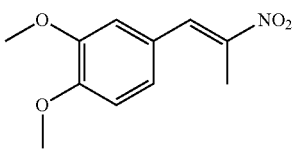

Figure 3:
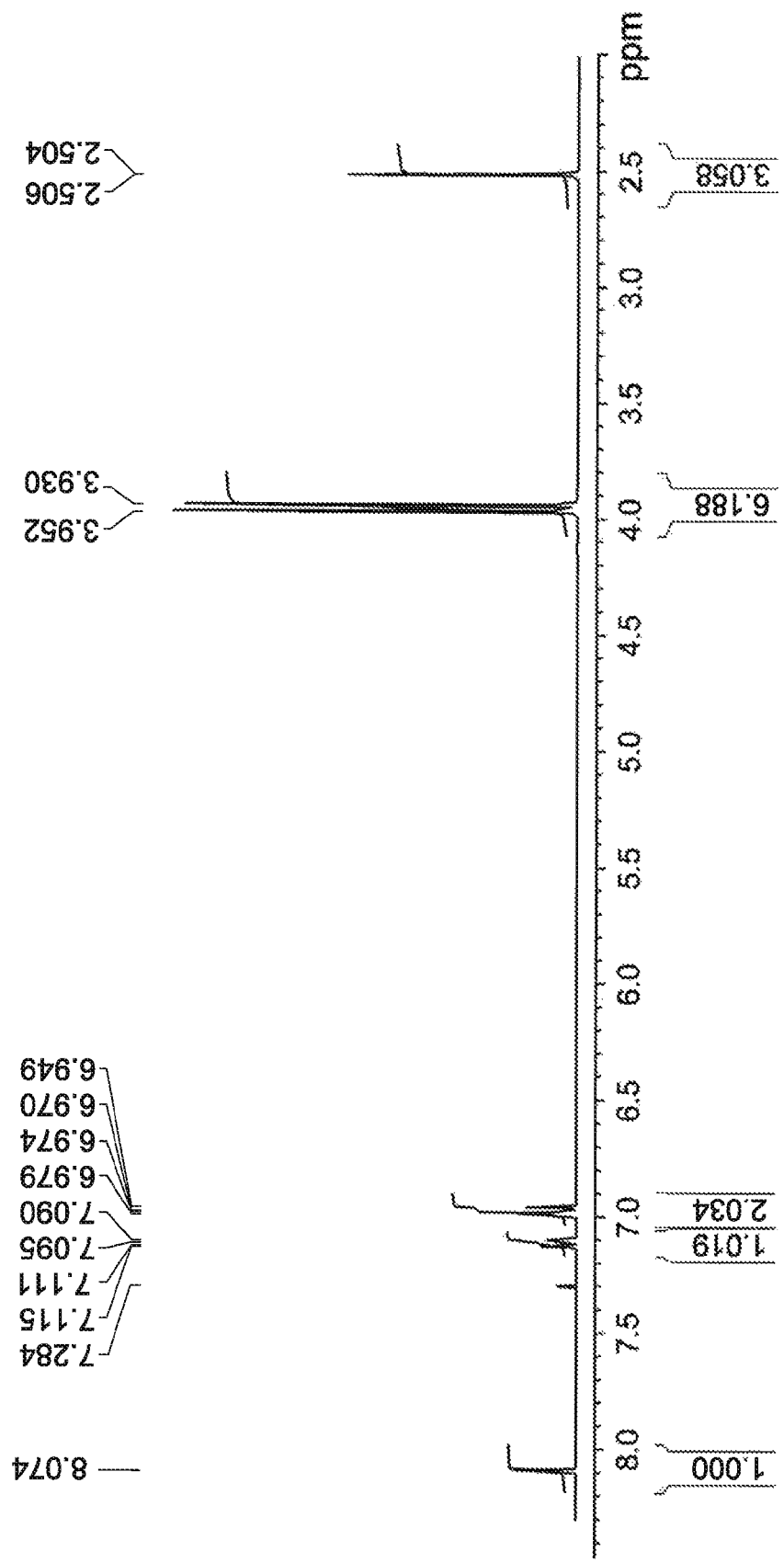

4.99 g (30.0 mmol) 3,4-dimethoxybenzaldehyde (Aldrich, Milwaukee, Wis.), 15.0 g (194 mmol) ammonium acetate (Fluka), and 70 g (930 Mmol) nitroethane, 98% (Aldrich) were combined in a 100 ml round bottom flask equipped with magnetic stirrer and nitrogen inlet. The reaction mixture was heated to 105° C. for 90 minutes and the solvent was removed under vacuum to give a dark yellow liquid which was recrystallized from cold methyl alcohol three times to give yellow-orange needles in 50% yield. 1H NMR spectra is shown in FIG. 3.

Example 4

Preparation of 1,2,3-trimethoxy-5-(2-nitroprop-1-enyl)benzene

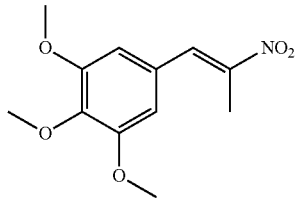

Figure 4:
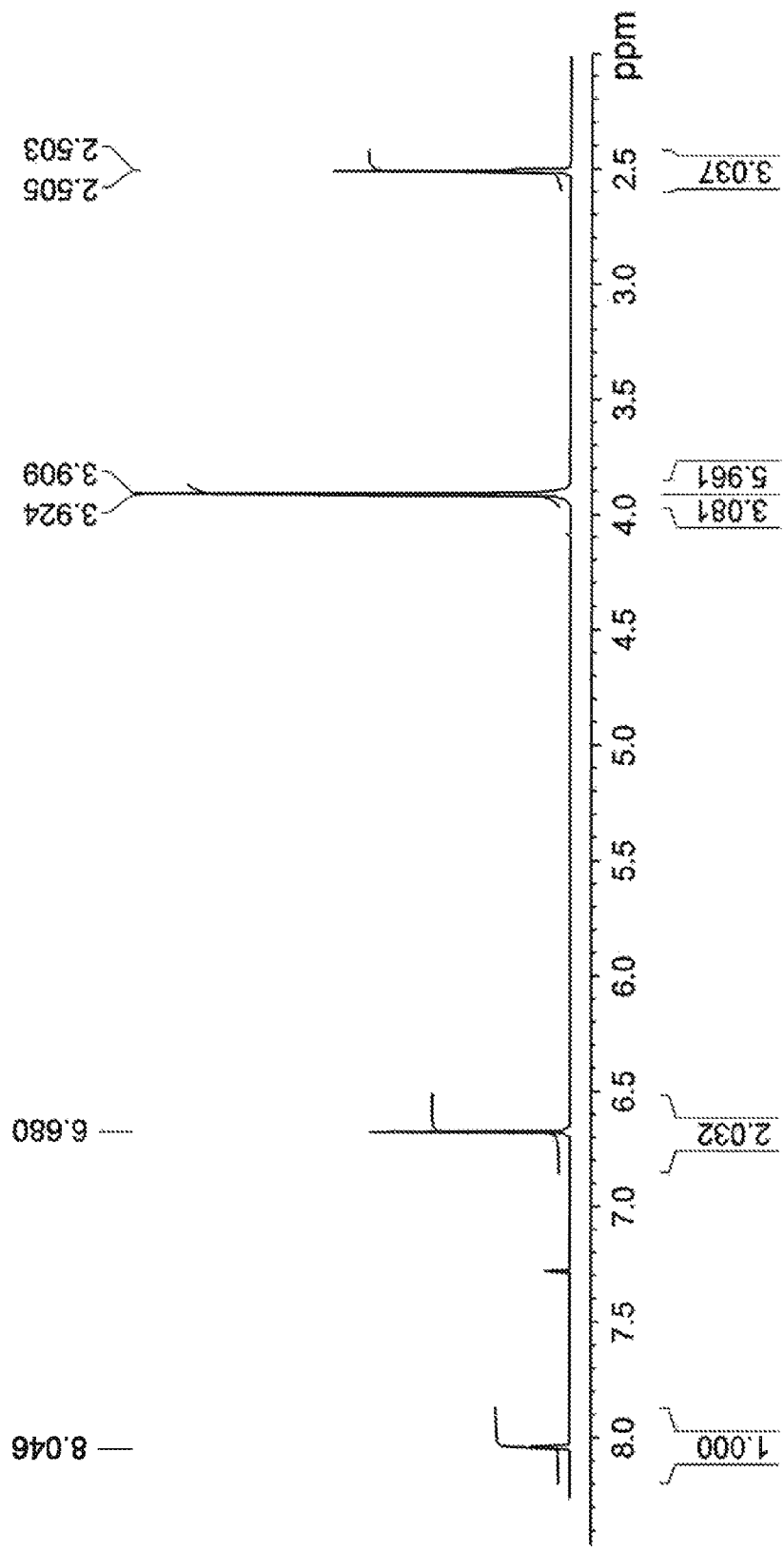

5.00 g (25.5 mmol) 3,4,5-trimethoxybenzaldehyde (Aldrich, Milwaukee, Wis.), 9.82 g (127 mmol) ammonium acetate (Fluka), and 50 g (670 Mmol) nitroethane, 98% (Aldrich) were combined in a 100 ml round bottom flask equipped with magnetic stirrer and nitrogen inlet. The reaction mixture was heated to 105° C. for 90 minutes and the solvent was removed under vacuum to give a crude product which was recrystallized from cold methyl alcohol three times to give yellow needles in 50% yield. 1H NMR spectra is shown in FIG. 4.

Example 5

Preparation of 4-(2-hydroxyethoxy)-3-methoxybenzaldehyde

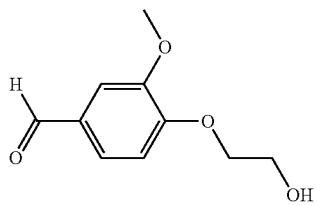

25.9 g (170 mmol) vanillin (Aldrich), 33.3 g (266 mmol) 2-bromoethanol (Aldrich), 35.2 g (255 mmol) potassium carbonate (Sigma-Aldrich), and 20 g molecular sieves (Aldrich) were combined in a 1 liter round bottom flask equipped with magnetic stirrer and nitrogen inlet. Acetone (600 ml) (Chromesolv for HPLC, >99.9%, Sigma-Aldrich) was added and the reaction mixture was refluxed for 16 hours using an external glycerol heating bath set to 65° C. The solids were filtered and the solvent was removed via rotary evaporation to yield a yellow oil. White crystals were obtained by recrystallization in ethyl alcohol at −20° C. (40% yield).

Example 6

Preparation of 2-(2-methoxy-4-(2-nitroprop-1-enyl) phenoxy)ethanol

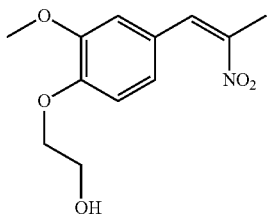

Figure 5:
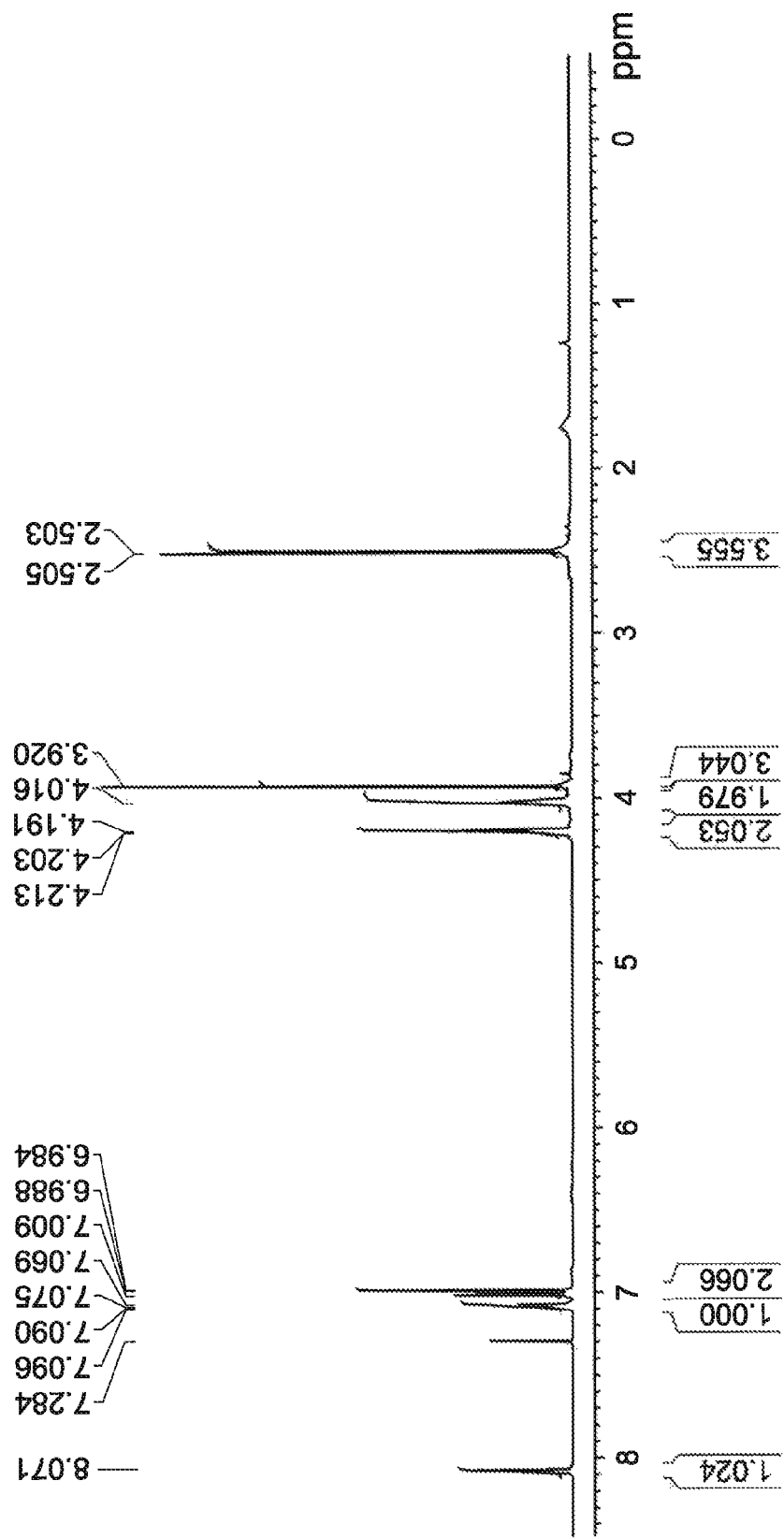

5.04 g (25.7 mmol) 4-(2-hydroxyethoxy)-3-methoxybenzaldehyde from Example 5, 9.80 g (127 mmol) ammonium acetate, 13.5 g dry molecular sieves (Aldrich, dried in 120 degrees Celcius oven), 82 g 2-propanol, and 83 g nitroethane were combined in a 200 ml round bottom flask equipped with magnetic stirrer and nitrogen inlet. The reaction mixture was refluxed for 90 minutes using an external heating bath set to 90° C., poured into 200 ml THF and then filtered. The solvent was removed via rotary evaporation and the crude product was recrystallized from 2-propanol (50% yield). 1H NMR spectra is shown in FIG. 5.

Example 7

Preparation of 2-(2-methoxy-4-(2-nitroprop-1-enyl) phenoxy)ethyl methacrylate

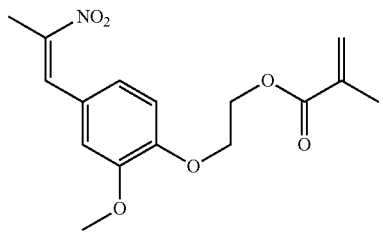

Figure 6:
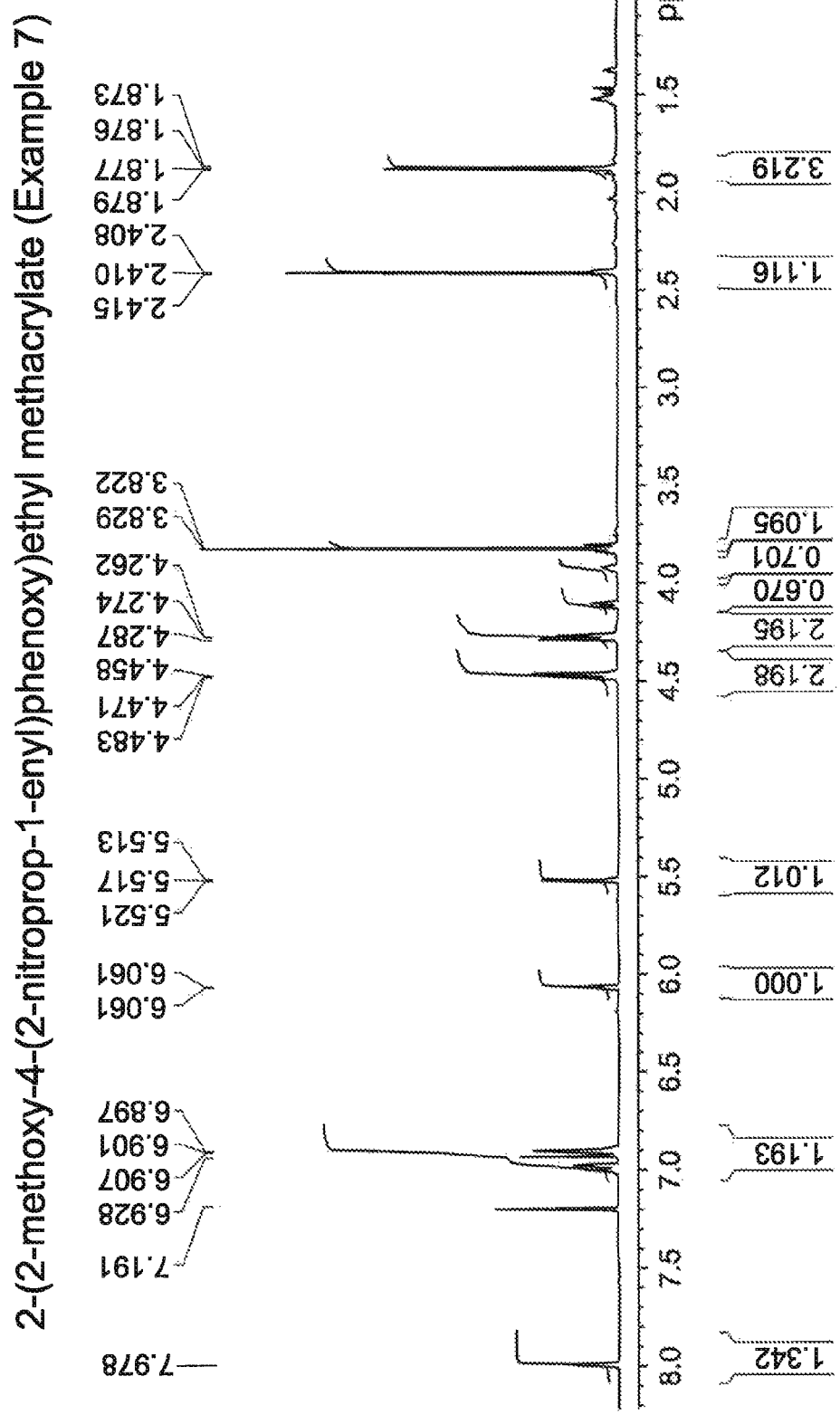
Figure 7:
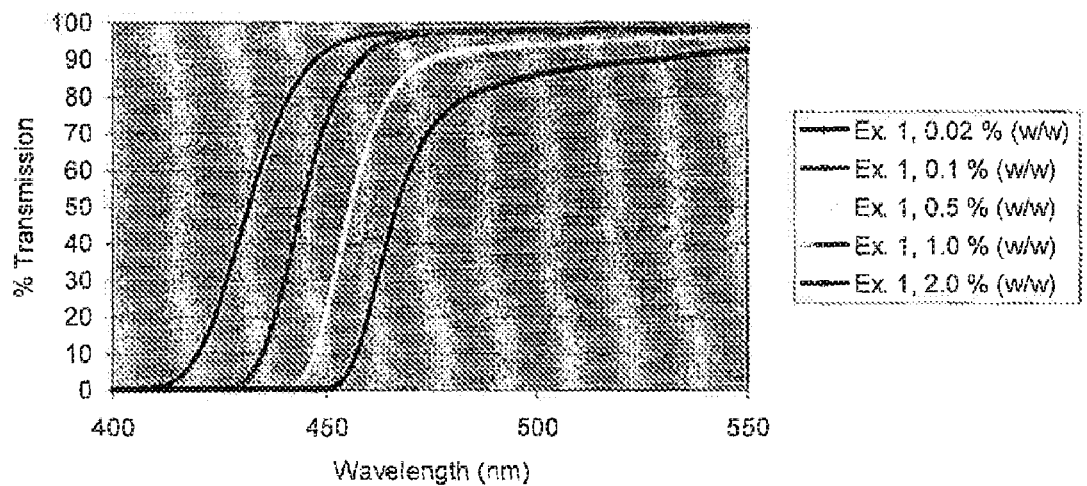
Figure 8:
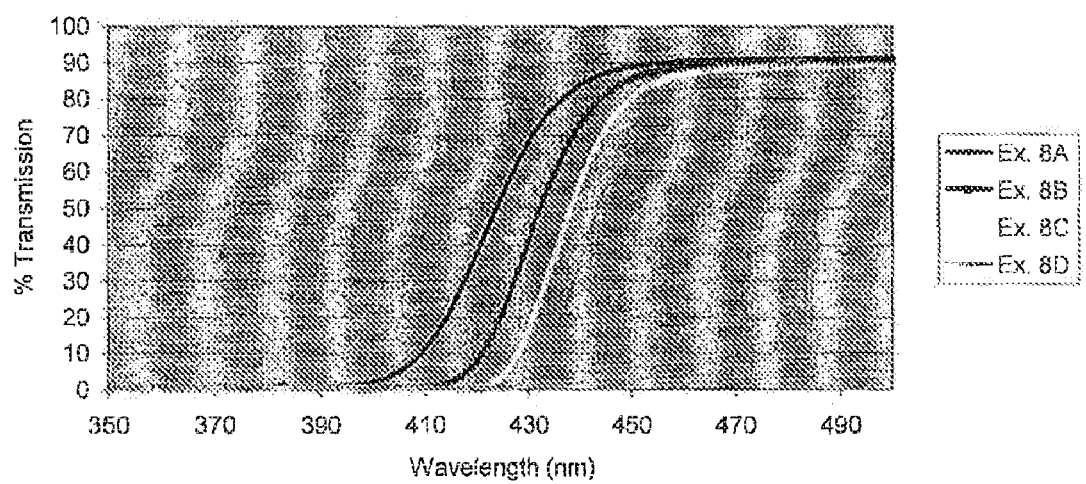

0.40 g (1.6 mmol) 2-(2-methoxy-4-(2-nitroprop-1-enyl) phenoxy)ethanol from Example 6 was dissolved to 10 ml anhydrous pyridine (Burdick & Jackson). 20 mg 4-methoxyphenol (MEHQ, Aldrich) and 0.54 g (3.5 mmol) methacrylic anhydride, 94% (Alfa Aesar) were added and the reaction mixture was heated using an external heating bath set at 70° C. for 1 hour. Methylene chloride (100 ml) was added and the organic layer was washed with 0.2 N HCl (500 ml×3), 0.15 M NaHCO$_3$ (500 ml×2) and deionized water (500 ml×1). The organic layer was dried over anhydrous Na$_2$SO$_4$, filtered, and the solvent was removed via rotary evaporation to yield an oil which was dissolved in ~5 ml methyl alcohol and cooled to −20° C. Within 30 minutes a yellow solid begin to settle to the bottom. The mixture was further cooled overnight at −20° C. to afford yellow needles in 40% yield. $^1$H NMR spectroscopy confirmed the presence of approximately 25 mol % of unreacted starting material. 1H NMR spectra is shown in FIG. 6.

Example 8

Ocular Lens Formulations

Figure 9:
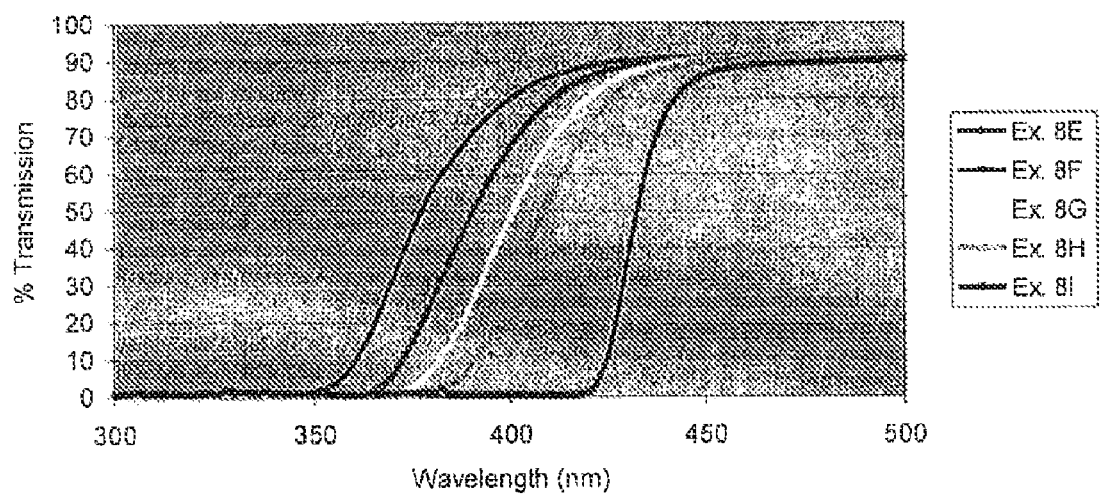
Figure 10:
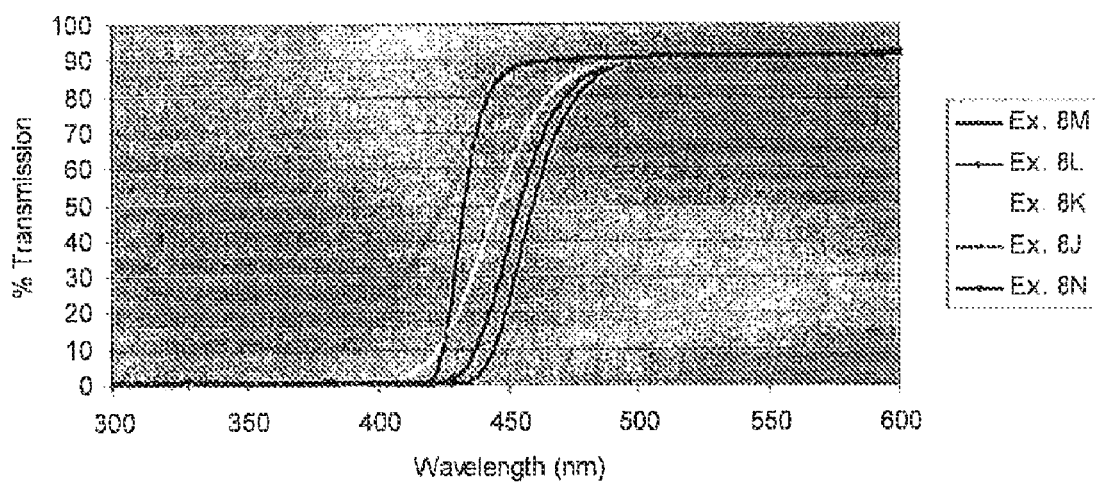
Figure 11:
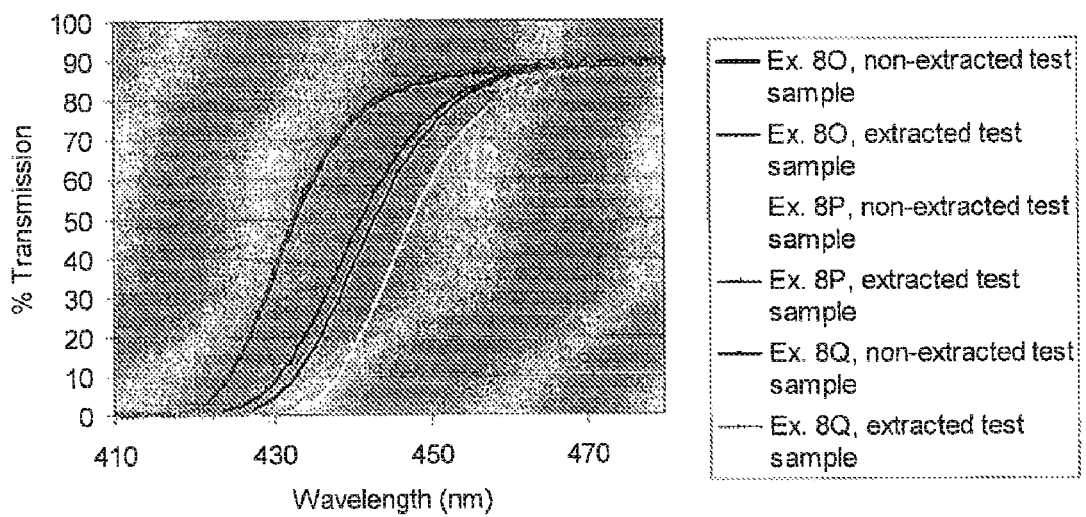

Model compounds from Examples 1 through 3 and reactive compound from Example 7 were formulated as shown in Tables 1 through 4. The UV/Vis spectra from 0.9 mm thick sample sections were collected and expanded between approximately 600 and 300 nm as shown in FIGS. 7 through 11. 3-(3-tert-butyl-4-hydroxy-5-(5-methoxy-2H-benzo[d][1,2,3]triazol-2-yl)phenoxy)propyl methacrylate was used as a control with 1.8% loading as shown in FIGS. 9 through 11. In FIG. 11, UV/Vis spectra of extracted and non-extracted test samples containing the reactive compound from Example 7 were compared. The reactive compound contained approximately 25 mol % of unreacted starting material. Thus, the transmission curves of the extracted samples were shifted slightly to the left due to the presence of less UV absorber after extraction.

In summary more favorable transmission curves were observed for samples 8O and 8P, which contained 0.75 wt. % and 1.5 wt. %, respectively, of the reactive compound. Control sample 8Q, which contained 1.8 wt. % of the control UV absorber, was not as efficient at blocking out higher wavelengths of violet light as shown in FIG. 11 and summarized in Table 5.

In the examples below,
PEA=2-phenylethyl acrylate
PEMA=2-phenylethyl methacrylate
Terg15S30-MA=methacrylate derivative of Tergitol™ 15S30
BDDA=1,4-butanediol diacrylate
AIBN=2,2'-azobis(2-methylpropionitrile)
Control=3-(3-tert-butyl-4-hydroxy-5-(5-methoxy-2H-benzo[d][1,2,3]-triazol-2-yl)phenoxy)propyl methacrylate
DEGDMA=diethylene glycol dimethacrylate

TABLE 1

| | Example (% w/w) | | | |
|---|---|---|---|---|
| Component | 8A | 8B | 8C | 8D |
| Ex 1 UV Absorber | 0.1 | 0.25 | 0.50 | 1.0 |
| PEA | 50.0 | 49.9 | 49.8 | 49.5 |
| PEMA | 44.0 | 43.9 | 43.8 | 43.6 |
| Terg15S30-MA | 5.0 | 5.0 | 5.0 | 5.0 |
| BDDA | 1.0 | 1.0 | 1.0 | 1.0 |
| AIBN | 0.5 | 0.5 | 0.5 | 0.5 |

TABLE 2

| | Example (% w/w) | | | | |
|---|---|---|---|---|---|
| Component | 8E | 8F | 8G | 8H | 8I |
| Ex 2 UV Absorber | 0.1 | 0.25 | 0.50 | 1.0 | 0 |
| Control UV absorber | 0 | 0 | 0 | 0 | 1.8 |
| PEA | 66.1 | 66.1 | 65.7 | 65.5 | 65.0 |
| PEMA | 30.4 | 30.4 | 30.4 | 30.3 | 30.0 |
| BDDA | 3.4 | 3.2 | 3.3 | 3.2 | 3.2 |
| AIBN | 0.5 | 0.5 | 0.5 | 0.5 | 0.5 |

TABLE 3

| | Example (% w/w) | | | | |
|---|---|---|---|---|---|
| Component | 8J | 8K | 8L | 8M | 8N |
| Ex 3 UV Absorber | 0.1 | 0.25 | 0.50 | 1.0 | 0 |
| Control UV absorber | 0 | 0 | 0 | 0 | 1.8 |
| PEA | 66.1 | 66.0 | 65.9 | 65.5 | 65.0 |
| PEMA | 30.5 | 30.5 | 30.4 | 30.2 | 30.0 |
| DEGDMA | 3.3 | 3.3 | 3.2 | 3.2 | 3.2 |
| Irgacure 819 | 0.2 | 0.2 | 0.2 | 0.2 | 0.2 |

TABLE 4

| | Example (% w/w) | | |
|---|---|---|---|
| Component | 8O | 8P | 8Q |
| Ex 7 UV Absorber | 0.75 | 1.5 | 0 |
| Control UV absorber | 0 | 0 | 1.8 |
| PEA | 65.7 | 65.2 | 65.0 |
| PEMA | 30.3 | 30.1 | 30.0 |
| BDDA | 3.2 | 3.2 | 3.2 |
| AIBN | 0.5 | 0.5 | 0.5 |

TABLE 5

| Example | Solvent Extraction Of Test Samples | Wavelength (nm) at 10% Transmission | Wavelength (nm) at 50% Transmission |
|---|---|---|---|
| 1 (0.02% w/w in chloroform, 10 mm path length) | — | 420 | 432 |
| 1 (0.1% w/w in chloroform, 10 mm path length) | — | 435 | 444 |
| 1 (0.5% w/w in chloroform, 10 mm path length) | — | 447 | 482 |
| 1 (1.0% w/w in chloroform, 10 mm path length) | — | 452 | 461 |
| 1 (2.0% w/w in chloroform, 10 mm path length) | — | 457 | 467 |
| 8A | No | 409 | 424 |
| 8B | No | 421 | 432 |
| 8C | No | 428 | 438 |
| 8D | No | 434 | 443 |
| 8E | No | 361 | 377 |
| 8F | No | 372 | 391 |
| 8G | No | 382 | 401 |
| 8H | No | 391 | 409 |
| 8I (control) | No | 425 | 433 |
| 8J | No | 383 | 426 |
| 8K | No | 423 | 446 |
| 8L | No | 438 | 455 |
| 8M | No | 445 | 460 |
| 8N (control) | No | 425 | 433 |
| 8O | No | 433 | 443 |
| 8P | No | 438 | 448 |
| 8Q (control) | No | 425 | 433 |
| 8O | Yes | 431 | 441 |
| 8P | Yes | 437 | 447 |
| 8Q (control) | Yes | 424 | 433 |

I claim:

1. An ophthalmic device material comprising (i) a UV absorber of formula [I]

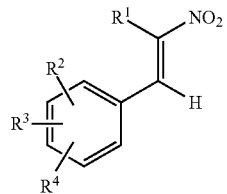

wherein:

R¹=H, CH₃, CH₃CH₂, (CH₃)₂CH, CH₃CH₂CH₂, HOCH₂, CH₂F, (CH₃)₃C, (CH₃)₃COCH₂, HOC(O)CHOCH₃, C(O)OH, CH₃OC(O)CHNH₂CH₂, CH₃CH₂OC(O)(CH₂)₂, (CH₃O)₂CH, (CH₃)₂CHOC(O), CH₃CH₂OC(O), CH₃OC(O), (CH₃CH₂O)₂CH, CH₃OC(O)(CH₂)₂, CH₃OC(O)CH₂NHCH₂, CH₃CH₂OC(O)CH₂, C₆H₅, C₆H₄OH, C₆H₅CH₂, C₆H₄CNCH₂, C₆H₄NO₂, C₆H₄NH₂CH₂, CH₂CH₂CHOC(O), CH₂=CHC(O)OCH₂, CH₂=CCH₃C(O)OCH₂, CH₂=CHC(O)OCH₂CH₂NHC(O), CH₂=CCH₃C(O)OCH₂CH₂NHC(O), CH₂=CHC(O)OCH₂CH₂NHC(O)OCH₂, or CH₂=CCH₃C(O)OCH₂CH₂NHC(O)OCH₂;

R², R³, and R⁴ independently =H, OH, CH₃O, CH₃CH₂O, CH₃CH₂CH₂O, (CH₃)₂CHO, (CH₃)₃CO, CH₃C(O)O, C₆H₅CH₂O, HOCH₂CH₂O, HOCH₂CH₂CH₂O, CH₂=CHC(O)OCH₂CH₂O, or CH₂=CCH₃C(O)OCH₂CH₂O CH₂=CCH₃C(O)O, CH₂=CHC(O)O, CH₂=CHC(O)OCH₂CH₂NHC(O), CH₂=CCH₃C(O)OCH₂CH₂NHC(O) CH₂=CHC(O)OCH₂CH₂NHC(O)OCH₂CH₂O, or CH₂=CCH₃C(O)OCH₂CH₂NHC(O)OCH₂CH₂O; or R²=H and R³ and R⁴ taken together form a methylenedioxy group; and provided that only one of R¹, R², R³, and R⁴ must contain a methacrylate or acrylate moiety, and (ii) a device-forming monomer selected from the group consisting of acrylic monomers and silicone-containing monomers.

2. The ophthalmic device material of claim 1 wherein the ophthalmic device material comprises from 0.1 to 5% (w/w) of the UV absorber of formula [I].

3. The ophthalmic device material of claim 2 wherein the ophthalmic device material comprises from 0.1 to 2% (w/w) of the UV absorber of formula [I].

4. The ophthalmic device material of claim 1 wherein the ophthalmic device material comprises an amount of the UV absorber of formula [I] sufficient to cause the device material to have light transmission properties such that the light transmitted through a 1 mm thick slab of the material at 10% transmission is 420-445 nm and at 50% transmission is 425-455 nm.

5. The ophthalmic device material of claim 1 wherein the ophthalmic device material comprises a device-forming monomer of formula [II]:

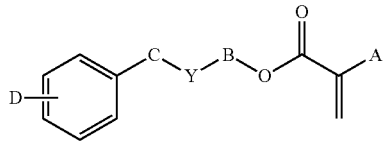

where in formula [II]:
A is H, CH₃, CH₂CH₃, or CH₂OH;
B is (CH₂)$_m$ or [O(CH₂)₂]$_z$;
C is (CH₂)$_w$;
m is 2-6;
z is 1-10;
Y is a bond, O, S, or NR', provided that if Y is O, S, or NR', then B is (CH₂)$_m$;
R' is H, CH₃, C$_n$H$_{2n'+1}$ (n'=1-10), iso-OC₃H₇, C₆H₅, or CH₂C₆H₅;
w is 0-6, provided that m+w≦8; and
D is H, C₁-C₄ alkyl, C₁-C₄ alkoxy, C₆H₅, CH₂C₆H₅ or halogen.

6. The ophthalmic device material of claim 5 wherein in formula [II]:
A is H or CH₃;
B is (CH₂)$_m$;
m is 2-5;
Y is a bond or O;
w is 0-1; and
D is H.

7. The ophthalmic device material of claim 6 wherein the ophthalmic device material comprises a monomer selected from the group consisting of: 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

8. The ophthalmic device material of claim 1 wherein the ophthalmic device material comprises a cross-linking agent.

9. The ophthalmic device material of claim 1 wherein the ophthalmic device material comprises a reactive blue-light absorbing compound.

10. An ophthalmic device comprising the ophthalmic device material of claim 1.

11. The ophthalmic device of claim 10 wherein the ophthalmic device is selected from the group consisting of an intraocular lens; a contact lens; a keratoprosthesis; and a corneal inlay or ring.

12. The ophthalmic device material of claim 1 wherein in formula [I] R¹=H, CH₃, HOCH₂, CH₃CH₂OC(O), CH₂=CHC(O)OCH₂, CH₂=CCH₃C(O)OCH₂, or CH₂=CHC(O)OCH₂CH₂NHC(O), CH₂=CCH₃C(O)OCH₂CH₂NHC(O).

13. The ophthalmic device material of claim 1 wherein in Formula [I] R², R³, and R⁴ independently =H, OH, CH₃O, CH₃CH₂O, CH₃C(O)O, C₆H₅CH₂O, CH₂=CHC(O)OCH₂CH₂O, or CH₂=CCH₃C(O)OCH₂CH₂O; or R²=H and R³ and R⁴ taken together form a methylenedioxy group; and provided that only one of R¹, R², R³, and R⁴ contains a methacrylate or acrylate, moiety.

14. The ophthalmic device material of claim 1 wherein in Formula [I] R¹ contains a methacrylate, acrylate, and R², R³ and R⁴ are independently selected from the group consisting of: 2-hydroxy-3-methoxy; 4-hydroxy-3-methoxy; 4-benzyloxy-3-methoxy; 4-acetoxy-3-methoxy; 3-ethoxy-4-hydroxy; 3-hydroxy-4-methoxy; 2-hydroxy-4-methoxy; 2-hydroxy-5-methoxy; 4-hydroxy-2-methoxy; 3,5-dimethoxy-4-hydroxy; 3-benzyloxy-4-methoxy; 2,3-dimethoxy; 2,4- dimethoxy; 2,5-dimethoxy; 2,6-dimethoxy; 3,4-dimethoxy; 3,5-dimethoxy; 4-acetoxy-3,5-dimethoxy; 2,3,4-trimethoxy; 2,4,5-trimethoxy; 2,4,6-trimethoxy; and 3,4,5-trimethoxy; or $R^3$ and $R^4$ taken together form a 2,3-(methylenedioxy) or 3,4-(methylenedioxy).

15. The ophthalmic device material of claim 1 wherein the UV absorber of Formula [I] is 2-(2-methoxy-4-(2-nitroprop-1-enyl)phenoxy)ethyl methacrylate.

* * * * *